(12) United States Patent
Gossweiler, III et al.

(10) Patent No.: US 8,665,238 B1
(45) Date of Patent: Mar. 4, 2014

(54) DETERMINING A DOMINANT HAND OF A USER OF A COMPUTING DEVICE

(71) Applicants: Richard Carl Gossweiler, III, Sunnyvale, CA (US); Hrishikesh Aradhye, Santa Clara, CA (US)

(72) Inventors: Richard Carl Gossweiler, III, Sunnyvale, CA (US); Hrishikesh Aradhye, Santa Clara, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 13/658,632

(22) Filed: Oct. 23, 2012

Related U.S. Application Data

(60) Provisional application No. 61/704,334, filed on Sep. 21, 2012.

(51) Int. Cl.
*G06F 3/041* (2006.01)

(52) U.S. Cl.
USPC ............................................... 345/173

(58) Field of Classification Search
USPC ................................................ 345/156–173
See application file for complete search history.

(56) References Cited

U.S. PATENT DOCUMENTS

| | | | |
|---|---|---|---|
| 5,402,152 A * | 3/1995 | Needham ..................... | 345/179 |
| 6,630,922 B2 | 10/2003 | Fishkin et al. | |
| 7,701,442 B2 | 4/2010 | Wong et al. | |
| 2004/0064597 A1* | 4/2004 | Trewin ........................ | 710/8 |
| 2006/0110203 A1* | 5/2006 | Grafton ....................... | 400/489 |
| 2006/0197750 A1* | 9/2006 | Kerr et al. .................... | 345/173 |
| 2010/0085317 A1* | 4/2010 | Park et al. .................... | 345/173 |
| 2010/0097331 A1* | 4/2010 | Wu .............................. | 345/173 |
| 2010/0162109 A1* | 6/2010 | Chatterjee et al. ........... | 715/702 |
| 2011/0057907 A1* | 3/2011 | Kim et al. .................... | 345/175 |
| 2011/0273378 A1* | 11/2011 | Alameh et al. ............... | 345/173 |

FOREIGN PATENT DOCUMENTS

EP      1255187 A2    11/2002

\* cited by examiner

*Primary Examiner* — William Boddie
*Assistant Examiner* — Carolyn R Edwards
(74) *Attorney, Agent, or Firm* — Shumaker & Sieffert, P.A.

(57) ABSTRACT

In one example, a method includes determining, by a computing device, a plurality of features. Each feature from the plurality of features may be usable to determine a dominant hand of a user of the computing device. The method also includes receiving, by the computing device, a plurality of input values, each input value from the plurality of input values corresponding to the respective plurality of features, and determining, using a probabilistic model and based at least in part on at least one input value from the plurality of input values corresponding to the respective feature from the plurality of features, a hand of the user as a dominant hand of the user. The method also includes generating, based at least in part on the determined dominant hand of the user, a graphical user interface for display at a presence-sensitive display operatively coupled to the computing device.

20 Claims, 6 Drawing Sheets

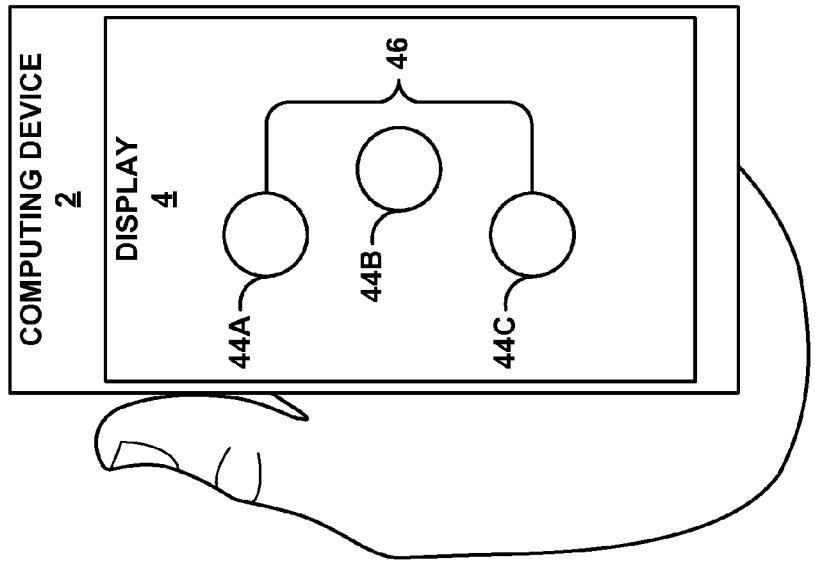
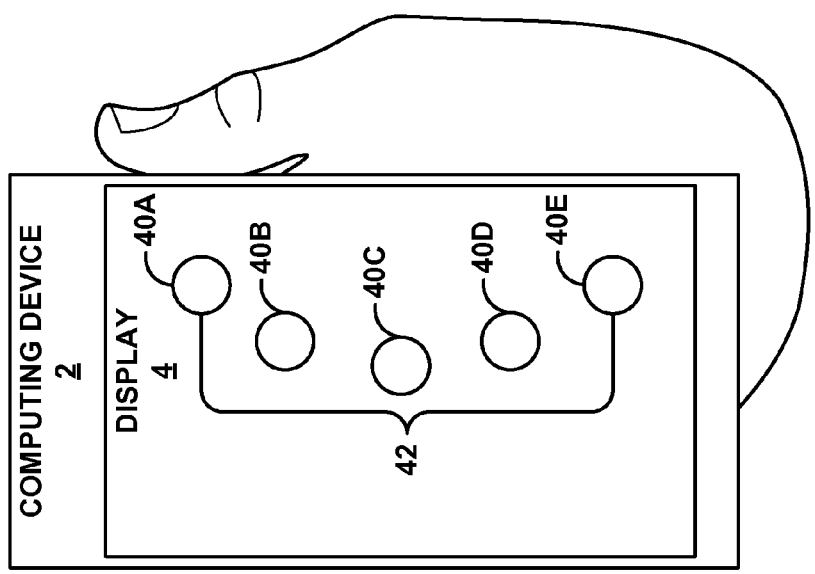
FIG. 3B
FIG. 3A

US 8,665,238 B1

DETERMINING A DOMINANT HAND OF A USER OF A COMPUTING DEVICE

BACKGROUND

Computing devices provide users with the ability to interact with processes and data using input and output devices. For example, a user may provide a user input to a computing device using a presence-sensitive display that displays a graphical user interface (GUI). The user input may cause the computing device to modify the execution of a process and/or data. Such processes may provide a user with the ability to access the Internet, play games, and play videos and music, as well as providing other various types of functionality.

In certain examples, the computing device may be a mobile computing device, such as a mobile phone (e.g., a smartphone) or tablet computer that the user may hold in his or her hand. As an example, a user may hold a mobile computing device in the user's right hand, and may provide user input gestures at a presence-sensitive display of the mobile computing device using the left hand of the user. Advancements in computing devices have enabled such devices to provide users with richer user experiences that include increasingly complex graphical user interfaces.

SUMMARY

In one example, a method includes determining, by a computing device, a plurality of features. Each feature from the plurality of features may be usable to determine a dominant hand of a user of the computing device. The method also includes receiving, by the computing device, a plurality of input values, each input value from the plurality of input values corresponding to a respective feature from the plurality of features, and determining, using a probabilistic model and based at least in part on at least one input value from the plurality of input values corresponding to the respective feature from the plurality of features, a hand of the user as a dominant hand of the user. The method also includes generating, based at least in part on the determined dominant hand of the user, a graphical user interface for display at a the presence-sensitive display operatively coupled to the computing device.

In one example, a computer-readable storage medium is encoded with instructions that, when executed, cause one or more processors of a computing device to perform operations including determining a plurality of features. Each feature from the plurality of features may be usable to determine a dominant hand of a user of the computing device. The computer-readable storage medium may be further encoded with instructions that, when executed cause the one or more processors to perform operations including receiving a plurality of input values, each input value from the plurality of input values corresponding to a respective feature from the plurality of features, determining, using a probabilistic model and based at least in part on at least one input value from the plurality of input values corresponding to the respective feature from the plurality of features, a hand of the user as a dominant hand of the user, and generating, based at least in part on the determined dominant hand of the user, a graphical user interface for display at a presence-sensitive display operatively coupled to the computing device.

In one example, a computing device includes one or more processors, a presence-sensitive display that is operatively coupled to the computing device, and one or more sensors. The one or more processors may be configured to determine a plurality of features. Each feature from the plurality of features may be usable to determine a dominant hand of a user of the computing device. The one or more processors may be further configured to receive, from the one or more sensors, a plurality of input values, each input value from the plurality of input values corresponding to a respective feature from the plurality of features, and determine, using a probabilistic model and based at least in part on at least one input value from the plurality of input values corresponding to the respective feature from the plurality of features, a hand of the user as a dominant hand of the user. The one or more processors may be further configured to generate, based at least in part on the determined dominant hand of the user, a graphical user interface for display at the presence-sensitive display.

The details of one or more examples of the disclosure are set forth in the accompanying drawings and the description below. Other features, objects, and advantages will be apparent from the description and drawings, and from the claims.

BRIEF DESCRIPTION OF DRAWINGS

FIGS. 3A and 3B are conceptual diagrams illustrating an example computing device that may be used to determine a dominant hand of a user and generate a graphical user interface based at least in part on the determined dominant hand, in accordance with one or more aspects of this disclosure.

DETAILED DESCRIPTION

Figure 1A:
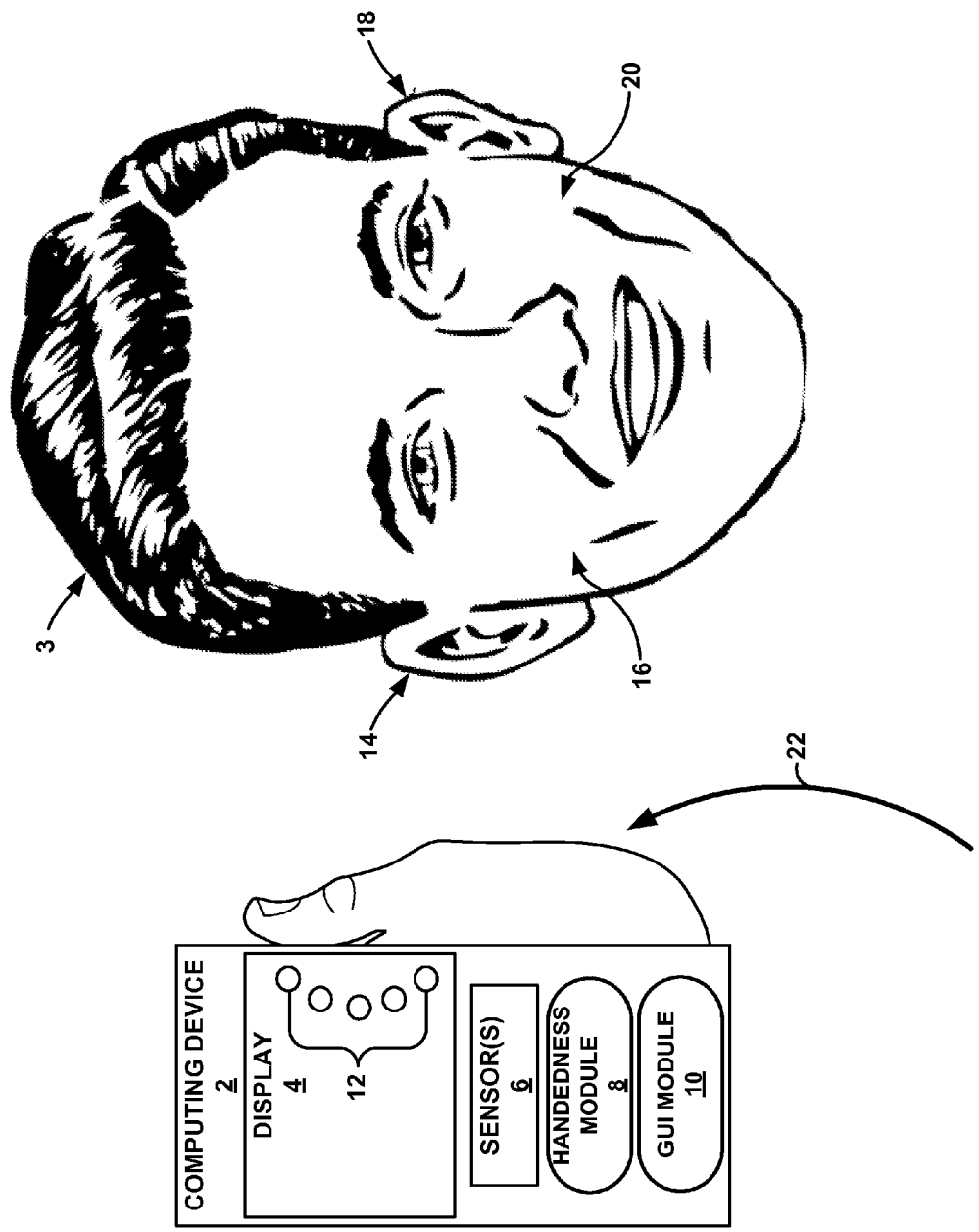
FIG. 1A is a conceptual diagram illustrating an example computing device that may be used to determine a dominant hand of a user and generate a graphical user interface based at least in part on the determined dominant hand, in accordance with one or more aspects of this disclosure.

In general, this disclosure is directed to techniques for determining a dominant hand of a user of a computing device to improve user interactions with a presence-sensitive display operatively coupled to the computing device. A computing device may output a graphical user interface (GUI) at a presence-sensitive display. The presence-sensitive display (e.g., a touch-sensitive screen) may enable a user to interact with graphical elements of the GUI by detecting user inputs in the form of gestures performed at or near the presence-sensitive display. For instance, a user may provide a touch gesture to select a graphical button control of the GUI. Advancements in computing devices have enabled such devices to provide increasingly complex GUIs. However, some presence-sensitive displays, such as those associated with mobile computing devices, may provide relatively small interaction surfaces with which to display a GUI and receive user input gestures. The combination of increasingly complex GUIs and the limited space provided by many presence-sensitive displays may increase the difficulty for a user to provide user input gestures to interact with the computing device. Moreover, users may typically be more accurate and quicker when providing such gestures using a dominant hand of the user than when using a non-dominant hand of the user.

Techniques of this disclosure may improve the ease with which a user can provide user input gestures (e.g., touch gestures) to interact with a GUI output at a presence-sensitive display of a computing device. According to various techniques of this disclosure, a computing device (e.g., a mobile computing device such as a mobile phone or tablet computer) may determine a dominant hand of the user. For instance, the computing device may receive a plurality of input values (e.g., acceleration information from an accelerometer of the computing device, physical orientation information from a gyroscope of the computing device, visual information from an image sensor of the computing device, etc.), each input from the plurality of inputs corresponding to a respective feature from a plurality of features that are usable to determine the dominant hand of the user. Such features may include, but are not limited to, acceleration information of a computing device, physical orientation of the computing device, visual information associated with the computing device, one or more user inputs detected at a presence-sensitive and/or touch-sensitive display device operatively coupled to the computing device, and the like.

The computing device may use a probabilistic model, such as a Bayesian network, to determine the dominant hand of the user based at least in part on the plurality of input values. For instance, the computing device may compare the received input values to corresponding baseline values determined with respect to known right-handed and/or left-handed users.

The computing device may generate, based at least in part on the determined dominant hand of the user, a GUI for display in a dominant hand visual configuration. As an example, the computing device may determine that a left hand of a user is the dominant hand of the user. In response, the computing device may generate a GUI in a dominant hand visual configuration that includes, in one example, graphical elements (e.g., one or more graphical button controls) positioned along a radius that follows a typical arc of a left thumb of a user holding a mobile computing device in the left hand of the user (e.g., a left-handed visual configuration). As such, the computing device may promote usability by facilitating user selection of graphical elements with the dominant thumb of the user.

In some examples, the computing device may determine, based at least in part on at least one input value from the plurality of received input values, that the user is currently holding the computing device with a non-dominant hand of the user. In response, the computing device may generate a GUI in a non-dominant hand visual configuration. For instance, the computing device may determine that a left hand of the user is a dominant hand of the user, and that the user is currently holding the computing device in a right hand of the user (i.e., a non-dominant hand of the user in this example). In such an example, the computing device may generate a GUI in a non-dominant hand visual configuration. In some examples, the non-dominant hand visual configuration includes graphical elements (e.g., one or more graphical button controls) positioned along a radius that follows a typical arc of a right thumb of a user holding a computing device in a right hand of the user (e.g., a right-handed visual configuration).

The non-dominant hand visual configuration may be different than the dominant hand visual configuration with respect to one or more of a size, shape, location, number of graphical elements generated for display, or other properties of the visual configuration. For instance, a non-dominant hand visual configuration may include fewer, but larger graphical elements to compensate for a tendency of users to be less accurate when providing user input gestures with a non-dominant hand of the user. As such, the computing device may promote improved usability by facilitating user selection of graphical elements with the non-dominant hand of the user.

FIG. 1A is a conceptual diagram illustrating an example computing device that may be used to determine a dominant hand of a user and generate a graphical user interface based at least in part on the determined dominant hand, in accordance with one or more aspects of this disclosure. As illustrated in FIG. 1, computing device 2 may include display 4, one or more sensors 6, handedness module 8, and graphical user interface (GUI) module 10. Examples of computing device 2 may include, but are not limited to, portable or mobile devices such as mobile phones (including smartphones), tablet computers, smart television platform, personal digital assistants (PDAs), and the like. As shown in the example of FIG. 1A, computing device 2 may be a mobile phone, such as a smartphone.

Display 4 may be a liquid crystal display (LCD), e-ink, organic light emitting diode (OLED), or other display. Display 4 may present the content of computing device 2 to a user. For example, display 4 may display the output of applications executed on one or more processors of computing device 2, confirmation messages, indications, or other functions that may need to be presented to a user.

In some examples, display 4 may provide some or all of the functionality of a user interface of computing device 2. For instance, as in the example of FIG. 1A, display 4 may be a touch-sensitive and/or presence-sensitive display that can display a GUI and detect input from a user in the form of user input gestures (e.g., touch gestures, swipe gestures, pinch gestures, and the like) using capacitive or inductive detection at or near the presence-sensitive display.

As illustrated in FIG. 1A, computing device 2 may include handedness module 8 and GUI module 10. GUI module 10 may perform one or more functions to receive input, such as one or more user input gestures detected at display 4. GUI module 10 may send such input to other components associated with computing device 2, such as handedness module 8 or other application(s) executing on one or more processors of computing device 2. GUI module 10 may also receive data from components associated with computing device 2, such as handedness module 8. Using the data, GUI module 10 may cause components associated with computing device 2, such as display 4, to provide output based on the data. For instance, GUI module 10 may receive data from handedness module 8 that causes GUI module 10 to display a GUI at display 4 to enable a user to interact with computing device 2.

As shown in FIG. 1A, GUI module 10 may generate a GUI for display at display 4 that includes one or more graphical elements, such as graphical elements 12. Graphical elements 12 may include any one or more graphical elements to enable a user to provide user input gestures to interact with computing device 2. For instance, graphical elements 12 may be graphical button controls, checkbox controls, slider controls, or other types of graphical control elements. As one example, graphical elements 12 may include one or more graphical button controls to enable a user to provide user input gestures to interact with an email application, at least portions of which execute on one or more processors of computing device 2. For instance, in such an example, graphical elements 12 may include a "compose" graphical button to enable a user to create a new email message, a "send" graphical button to enable a user to send an email message, an "archive" graphical button to enable a user to archive one or more email messages, and the like. Other examples of graphical elements 12 are possible, and the non-limiting example above is provided only for purposes of discussion.

Graphical elements 12 may be the same or different types of graphical elements. For instance, in some examples, at least one of graphical elements 12 may be a graphical button control and at least one of graphical elements 12 may be a graphical checkbox control. In certain examples, each of graphical elements 12 may be the same type of graphical elements, such as when each of graphical elements 12 is a graphical button control.

GUI module 10 may generate a GUI for display at display 4 in various visual configurations. For instance, GUI module 10 may generate a GUI for display in a right-handed visual configuration. In certain examples, GUI module 10 may generate a GUI for display in a left-handed visual configuration that is different from the right-handed visual configuration. In some examples, GUI module 10 may generate a GUI for display in a dominant hand visual configuration that is different from a non-dominant hand visual configuration. The dominant hand visual configuration may be either a right-handed visual configuration or a left-handed visual configuration. Similarly, the non-dominant hand visual configuration may be either a right-handed visual configuration or a left-handed visual configuration. GUI module 10 may, in some examples, generate a GUI for display at a display device operatively coupled to computing device 2 (e.g., display 4) based at least in part on a determination by computing device 2 of a dominant hand of a user interacting with computing device 2. For example, GUI module 10 may receive data from handedness module 8 indicating a dominant hand of a user. GUI module 10 may generate the GUI for display at display 4 based at least in part on the data received from handedness module 8 indicating the dominant hand of the user.

Handedness module 8 may determine a plurality of features, each of which is usable to determine a dominant hand of a user. Examples of such features include, but are not limited to, a physical orientation of computing device 2, acceleration information of computing device 2, indications of one or more user inputs detected at display 4 (e.g., a presence-sensitive and/or touch-sensitive display), visual information of an image sensor (e.g., a camera device) of computing device 2, and the like.

Physical orientation information of computing device 2 may be usable to determine a dominant hand of a user. For instance, computing device 2 may be a mobile computing device such as a mobile phone or tablet computer. In such examples, a user, such as user 3, may hold computing device 2 in the user's hand. In the illustrated example of FIG. 1A, user 3 holds computing device 2 in a right hand of user 3. In some examples, such as when computing device 2 includes a mobile phone, user 3 may hold computing device 2 against the side of his or her head while using computing device 2 for telephonic communications. A right-handed user (i.e., a user whose right hand is dominant over a non-dominant left hand) may typically hold a mobile computing device in a right hand of the user against the right side of his or her head while using the mobile computing device for telephonic communications. Similarly, a left-handed user (i.e., a user whose left hand is dominant over a non-dominant right hand) may typically hold a mobile computing device in a left hand of the user against the left side of his or her head while using the mobile computing device for telephonic communications. As such, physical orientation information of computing device 2 while computing device 2 is being used for telephonic communications may be usable to determine a dominant hand of a user. That is, physical orientation information indicating that computing device 2 is held against a right side of a head of a user may indicate that a right hand of the user is a dominant hand of the user. Physical orientation information indicating that computing device 2 is held against a left side of a head of a user may indicate that a left hand of the user is a dominant hand of the user.

In the example of FIG. 1A, user 3 may hold computing device 2 against right ear 14 (i.e., a right ear of user 3) and right cheek 16 (i.e., a right cheek of user 3) while using computing device 2 for telephonic communications. Similarly, user 3 may hold computing device 2 against left ear 18 (i.e., a left ear of user 3) and left cheek 20 (i.e., a left cheek of user 3) while using computing device 2 for telephonic communications. As discussed in further detail with respect to the illustrated example of FIG. 1B, a physical orientation of computing device 2 while the user is holding computing device 2 against the side of his or her head may typically differ depending upon whether computing device 2 is being held against right ear 14 and right cheek 16 or whether computing device 2 is being held against left ear 18 and left cheek 20. That is, due in part to typical anatomical features of the human head, an angle of a physical orientation of computing device 2 with respect to the ground while computing device 2 is held against right ear 14 and right cheek 16 may be substantially opposite an angle of a physical orientation of computing device 2 with respect to the ground while computing device 2 is held against left ear 18 and left cheek 20.

In addition, physical orientation information of computing device 2 when computing device 2 detects one or more user input gestures at or near display 4 (e.g., a presence-sensitive display) may be usable to determine a dominant hand of user 3. For instance, a user may hold a mobile computing device in a dominant hand of the user while providing user input gestures with a thumb of the dominant hand of the user. In some examples, a user may hold a mobile computing device in a non-dominant hand of the user while providing user input gestures with a dominant hand of the user (e.g., with a finger of the dominant hand, or other input unit, such as a pen, stylus, etc. held in the dominant hand of the user).

While holding the mobile computing device in one hand, a user may typically hold the mobile computing device at a slight angle toward the opposite side of the user. For instance, a user holding a mobile computing device in a left hand of the user and providing user input gestures with a right hand of the user or a left thumb of the user may typically hold the mobile computing device such that a presence-sensitive display of the mobile computing device is angled toward the right side of the user. Similarly, a user holding a mobile computing device in a right hand of the user and providing user input gestures with a left hand of the user or a right thumb of the user may typically hold the mobile computing device such that a presence-sensitive display of the mobile computing device is angled toward the left side of the user. As such, physical orientation information of computing device 2 while computing device 2 detects one or more user input gestures (e.g., touch gestures, swipe gestures, pinch gestures, etc.) may be usable to determine a dominant hand of the user.

In certain examples, visual information from an image sensor of computing device 2 may be usable to determine a dominant hand of user 3. As discussed above, a right-handed user may typically hold a mobile computing device in a right hand of the user against the right side of his or her head while using the mobile computing device for telephonic communications. Similarly, a left-handed user may typically hold a mobile computing device in a left hand of the user against the left side of his or her head while using the mobile computing device for telephonic communications. As such, visual information indicating that computing device 2 is held against a right side of a user's head may indicate that a right hand of the user is a dominant hand of the user. Visual information indicating that computing device 2 is held against a left side of a user's head may indicate that a left hand of the user is a dominant hand of the user.

Such visual information may represent an anatomical feature of the user's head. For instance, the anatomical feature may include at least a portion of the side of the user's head. In some examples, the anatomical feature may include at least a portion of an ear of the user. For instance, in the example of FIG. 1A, the visual information may include at least a portion of right ear 14 or left ear 18. Because at least the outer edge of right ear 14 curves in an opposite direction to that of left ear 18, visual information representing a portion of right ear 14 or left ear 18 may be usable to determine whether computing device 2 is held against a right side or a left side of the head of user 3. Hence, because a right-handed user may typically hold computing device 2 against a right side of the user's head, and a left-handed user may typically hold computing device 2 against a left side of the user's head, the visual information may be usable to determine a dominant hand of the user.

Acceleration information of computing device 2 may be usable to determine a dominant hand of user 3. For instance, as discussed above, while using a mobile computing device for telephonic communications, a user may typically hold the mobile computing device in a dominant hand of the user against a dominant side of the user's head. As such, an acceleration profile resulting from the motion of the mobile computing device as the user moves the mobile computing device to the side of the user's head may differ depending upon whether the user moves the mobile computing device to the right side of the user's head or whether the user moves the mobile computing device to the left side of the user's head.

For example, as in the conceptual illustration of FIG. 1A, user 3, holding computing device 2 in a right hand, may move computing device 2 to the right side of the head of user 3 in motion 22. The acceleration profile of computing device 2 defined by motion 22 may typically differ from an acceleration profile defined by a similar motion (not illustrated) in which user 3 moves computing device 2 to the left side of the head of user 3. For instance, as one example, when moving computing device 2 from a user's pocket to the right side of the head of the user (e.g., to right ear 14 and right cheek 16 of user 3), the user may move computing device 2 along a path that arcs first toward the middle of the user's body then toward the right side of the user's body. In contrast, when moving computing device 2 from a user's pocket to the left side of the head of the user (e.g., to left hear 18 and left cheek 20 of user 3), the user may move computing device 2 along a path that arcs first toward the middle of the user's body then toward the left side of the user's body. As such, because the acceleration profile resulting from each path may differ, acceleration information of computing device 2 may be usable to determine a dominant hand of the user.

One or more user inputs detected at or near display 4 (e.g., a presence-sensitive and/or touch-sensitive display operatively coupled to computing device 2) may be usable to determine a dominant hand of user 3. For example, handedness module 8 may determine that a user input detected at or near display 4 indicates that display 4 is in contact with a cheek of user 3. For instance, handedness module 8 may compare an area of display 4 that detects the presence of an input unit to a threshold value. Handedness module 8 may determine that the detected user input indicates that display 4 is in contact with a cheek of user 3 when the area of display 4 that detects the presence of an input unit is greater than the threshold value. The threshold value may be a percentage of the total area of display 4, such as twenty-five percent, thirty-five percent, fifty percent, or other percentages of the total area of display 4. In certain examples, the threshold value may be user configurable.

The user input detected at or near display 4 indicating that display 4 is in contact with a cheek of user 3 may be usable to determine a dominant hand of user 3. For example, user 3 may hold computing device 2 to right ear 14 and right cheek 16 when using computing device 2 for telephonic communications. In such an example, display 4 may detect a user input indicating that right cheek 16 is in contact with display 4. Similarly, user 3 may hold computing device 2 to left ear 18 and left cheek 20 when using computing device 2 for telephonic communications. In such an example, display 4 may detect a user input indicating that left cheek 20 is in contact with display 4.

The profile of an area of display 4 that is in contact with right cheek 16 may typically differ from a profile of an area of display 4 that is in contact with left cheek 20. For example, a profile of an area of display 4 that is in contact with right cheek 16 may include an upper-left region of display 4 but not a lower-right region of display 4. The upper-left region and lower-right regions of display 4 may be considered upper-left and lower-right regions from the perspective of a user viewing display 4. That is, when user 3 holds computing device 2 to right ear 14 and right cheek 16 (e.g., when using computing device 2 for telephonic communications), display 4 may detect a user input at an upper-left region of display 4. However, in such an example, display 4 may typically not detect a user input at a lower-right region of display 4. In contrast, in examples where user 3 holds computing device 2 to left ear 18 and left cheek 20, display 4 may detect a user input at an upper-right region of display 4, but may not detect a user input at a lower-left region of display 4.

Handedness module 8 may analyze the touch region of the received user input at display 4, and may determine that user 3 may be holding computing device 2 to right ear 14 and right cheek 16 when an area of display 4 that is in contact with an input unit is greater than a threshold value (e.g., indicating a cheek-press user input) and when a region of display 4 that detects the user input includes upper-left region of display 4 but does not include a lower-right region of display 4. Handedness module 8 may determine that such a detected user input at display 4 indicates that a right hand of the user may be a dominant hand of the user. Similarly, handedness module 8 may determine that user 3 may be holding computing device 2 to left ear 18 and left cheek 20 when an area of display 4 that is in contact with an input unit is greater than a threshold value (e.g., indicating a cheek-press user input) and when a region of display 4 that detects the user input includes an upper-right region of display 4 but does not include a lower-left region of display 4. Handedness module 8 may determine that such a detected user input indicates that a left hand of the user may be a dominant hand of the user.

In certain examples, a frequency at which user inputs are detected at a portion of display 4 (e.g., a presence-sensitive and/or touch-sensitive display) may be usable to determine a dominant hand of a user. For example, a user may typically hold a mobile computing device in a dominant hand of a user and provide user input gestures (e.g., touch gestures, swipe gestures, etc.) with a thumb of the dominant hand of the user. As such, a frequency at which user input gestures are detected at a portion of the presence-sensitive display corresponding to the dominant hand of the user (e.g., a right portion of display 4 corresponding to a dominant right hand of a user or a left portion of display 4 corresponding to a dominant left hand of a user) may be greater than a frequency at which user input gestures are detected at a portion of the presence-sensitive display corresponding to the non-dominant hand of the user. That is, because of the limited reach of the user's thumb, a user may provide a greater proportion of user input gestures at locations of the presence-sensitive display that are closest to the thumb of the hand holding the mobile computing device.

As an example, user 3 may be a right-handed user. As such, user 3 may typically hold computing device 2 in a right hand and provide user input gestures with a thumb of the right hand. Because of the limited reach of the thumb, user 3 may provide user input gestures more frequently at a right portion of display 4 than at a left portion of display 4. Similarly, in examples when user 3 is a left-handed user, user 3 may typically hold computing device 2 in a left hand and provide user input gestures with a thumb of the left hand. As such, user 3 may provide user input gestures more frequently at a left portion of display 4 than at a right portion of display 4.

Handedness module 8 may determine a frequency at which user input gestures are detected at portions of display 4 over time, such as over a time period of one hour, three hours, one day, or other time periods. Handedness module 8 may, in certain examples, determine a histogram (e.g., a "heat map") representing the frequency at which user input gestures are detected with respect to portions of display 4. Handedness module 8 may determine that a histogram indicating a greater frequency of received user input gestures at a right portion of display 4 than at a left portion of display 4 may indicate that a right hand of user 3 is a dominant hand of user 3. Similarly, handedness module 8 may determine that a histogram indicating a greater frequency of received user input gestures at a left portion of display 4 than at a right portion of display 4 may indicate that a left hand of user 3 is a dominant hand of user 3.

In some examples, a location of display 4 at which user input gestures (e.g., touch gestures) are detected as compared to a region of a selectable object displayed at display 4 may be usable to determine a dominant hand of a user. For example, GUI module 10 may cause display 4 to output one or more selectable objects, such as a graphical button, graphical slider control, and the like. A user providing a gesture (e.g., a touch gesture) at display 4 with a right hand of the user to select one of the selectable objects may typically provide the gesture at a location of display 4 that is slightly left of the selectable object from the perspective of a user viewing display 4. That is, when providing a gesture to select an object displayed at display 4, a user providing such a gesture with a right hand may typically provide the gesture at a location of display 4 that is biased toward the left side of the selectable object. Similarly, a user providing such a gesture with a left hand may typically provide the gesture at a location of display 4 that is slightly right of, or biased toward the right side of the selectable object.

Handedness module 8 may determine a frequency at which user input gestures to select a selectable object displayed at display 4 are biased toward the left of the selectable object and biased toward the right of the selectable object. Handedness module 8 may determine that a higher frequency of user input gestures biased toward the left of selectable objects indicates that a right hand of the user is a dominant hand of the user. Similarly, handedness module 8 may determine that a higher frequency of user input gestures biased toward the right of selectable objects indicates that a left hand of the user is a dominant hand of the user.

In certain examples, the speed and accuracy with which user input gestures are detected to select a plurality of selectable objects may be usable to determine a dominant hand of the user. For instance, a user may typically be quicker and more accurate when providing user input gestures with a dominant hand of the user than with a non-dominant hand of the user. As one example, handedness module 8 may cause GUI module 10 to output a GUI to determine the speed and accuracy with which a user provides user input gestures to select a plurality of selectable objects using a left hand of the user and using a right hand of a user.

For instance, handedness module 8 may cause GUI module 10 to output a GUI that includes a series of selectable objects sequentially output at display 4 over a period of time. The series of selectable objects may be displayed in succession at varying (e.g., random) locations of display 4, each of the selectable objects output for a threshold amount of time. For instance, the selectable objects may be displayed as "bubbles," each of the bubbles output at display 4 for a threshold amount of time, such as one second, five hundred milliseconds, two hundred and fifty milliseconds, or other threshold amounts of time. As an example, the GUI may first request the user to select the objects with a right hand of the user, then to select the objects with a left hand of the user. Handedness module 8 may determine characteristics of received user input gestures to select the selectable objects with respect to each of the right and left hands of the user. For instance, handedness module may determine the number of objects successfully selected with each hand, an average time between when a selectable object is displayed and a user input gesture is received to select the object with respect to each hand of the user, or other characteristics.

The determined characteristics of the detected user input gestures with respect to each of the left and right hands of the user may be usable to determine the dominant hand of the user. For instance, handedness module 8 may determine that a greater number of successfully selected objects with a right hand than with a left hand may indicate that a right hand of the user is a dominant hand of the user. Conversely, handedness module 8 may determine that a greater number of successfully selected objects with a left hand than with a right hand may indicate that a left hand of the user is a dominant hand of the user. Similarly, handedness module 8 may determine that a lower average time to select the selectable objects with a right hand than with a left hand may indicate that a right hand is a dominant hand of the user. Handedness module 8 may determine that a lower average time to select the selectable objects with a left hand than with a right hand may indicate that a left hand is a dominant hand of the user.

As such, computing device 2 may determine a plurality of features, each of which is usable to determine a dominant hand of the user. Computing device 2 may receive a plurality of input values, each input value from the plurality of input values corresponding to a respective feature from the plurality of features. For example, as illustrated in FIG. 1A, computing device 2 may include one or more sensors 6. Examples of one or more sensors 6 include, but are not limited to, accelerometers, gyroscopes, magnetometers, audio input devices (e.g., a microphone), image sensors (e.g., an image sensor associated with a camera device of computing device 2), and proximity sensors. Computing device 2 may receive a plurality of inputs from one or more sensors 6, such as acceleration information from one or more accelerometers of computing device 2, physical orientation information from one or more gyroscopes of computing device 2, visual information from one or more image sensors of computing device 2, audio information from one or more audio input devices of computing device 2, physical orientation information from one or more magnetometers of computing device 2, and information from one or more proximity sensors of computing device 2 indicating physical proximity of computing device 2 to another object.

Handedness module 8 may determine, using a probabilistic model and based at least in part on at least one input value from the plurality of input values corresponding to the respective feature from the plurality of features, a hand of the user as a dominant hand of the user. Non-limiting examples of such a probabilistic model include machine learning models such as Bayesian networks, artificial neural networks, support vector machines, as well as other probabilistic models. For example, using the probabilistic model, handedness module 8 may compare input values determined from one or more sensors 6 to corresponding baseline values determined with respect to known right-handed and/or left-handed users.

For instance, during a ground-truth collection phase, input values corresponding to one or more features from the plurality of features (e.g., physical orientation information, acceleration information, visual information, user input information detected at a presence-sensitive and/or touch-sensitive display device operatively coupled to the computing device, etc.) may be determined with respect to known right-handed and/or left-handed users. The input values determined with respect to the known right-handed and/or left-handed users may be used to determine one or more baseline values, each baseline value corresponding to a respective feature from the plurality of features. The baseline values may serve as a basis for comparison against which handedness module 8 may compare received inputs from one or more sensors 6 using the probabilistic model. For instance, handedness module 8 may determine a feature vector including the plurality of features, each of which is usable to determine a dominant hand of the user. Handedness module 8 may compare an input vector including a plurality of inputs determined from one or more sensors 6 to the feature vector including the baseline values. Handedness module 8 may determine a dominant hand of the user based at least in part on the comparison.

As an example, during the ground-truth collection phase, known right-handed and/or known left-handed users may be asked to use a computing device, such as computing device 2, in various ways. For instance, such users may be asked to interact with a GUI output at a presence-sensitive display operatively coupled to the computing device (e.g., display 4), such as by providing user input gestures to enter textual strings, select various selectable objects (e.g., button controls), and the like. Similarly, such users may be asked to use the computing device for telephonic communications, such as by moving the computing device to either the left or right side of the user's head. For each of the known right-handed and left-handed users, input values corresponding to a plurality of features of the feature vector may be recorded. For instance, physical orientation information received from a gyroscope of the computing device, acceleration information received from one or more accelerometers of the computing device, and visual information received from one or more image sensors of the computing device (e.g., visual information including a visual representation of an anatomical feature of the user's head, such as an ear of the user) may be recorded. Similarly, information associated with one or more user inputs detected at a presence-sensitive and/or touch-sensitive display device operatively coupled to the computing device may be determined, such as a frequency at which user input gestures are received at one or more portions of the display, a portion of the display that detects a user input indicating that the display is in contact with a cheek of the user, and the like.

In certain examples, a baseline feature vector (e.g., a stereotype) may be established using the recorded inputs. For instance, the baseline feature vector may be determined using an average of the recorded inputs associated with each feature, a weighted average of the recorded inputs, or other central tendency techniques to establish a baseline feature vector for at least one of a stereotypical right-handed and left-handed user.

Using the probabilistic model, handedness module 8 may compare a plurality of received inputs corresponding to the plurality of features of the baseline feature vector to determine a dominant hand of the user. For instance, in certain examples, handedness module 8 may determine an angle in n-dimensional space between the n-dimensional baseline feature vector and n-dimensional input feature vector, where "n" represents the number of distinct features of each of the two feature vectors. Therefore, in some examples, rather than determine the dominant hand of the user based upon only one type of input (e.g., only one of physical orientation information, acceleration information, or visual information associated with the computing device), computing device 2 may determine the dominant hand of the user based at least in part on the plurality of input values corresponding to the plurality of features. As such, techniques of this disclosure may increase the certainty with which a computing device may determine the dominant hand of a user based upon input values determined from one or more sensors of the computing device. Moreover, because the baseline values may be adjusted based upon further observations with respect to the user or other known right-handed or left-handed users, the techniques may enable the computing device to further increase the certainty with which the computing device may determine the dominant hand of any particular user.

GUI module 10 may generate, based at least in part on the determined dominant hand of the user, a GUI for display at a display device operatively coupled to computing device 2 (e.g., display 4). As one example, handedness module 8 may determine that a right hand is a dominant hand of user 3. In such an example, GUI module 10 may generate a right-handed GUI for display at display 4. For instance, as illustrated in FIG. 1A, GUI module 10 may generate a GUI that includes one or more graphical elements 12 arranged in a right-handed visual configuration. In some examples, the right-handed visual configuration may include a visual layout of graphical elements 12 such that graphical elements 12 are positioned at locations of display 4 along an arc that follows a radius reachable by a right thumb of user 3. That is, as illustrated in FIG. 1A, GUI module 10 may generate the right-handed GUI such that graphical elements 12 are positioned at a right portion of display 4 along an arc that follows a radius of a typical motion of a right thumb of user 3 as user 3 moves his or her right thumb between a top portion of display 4 and a bottom portion of display 4.

As another example, handedness module 8 may determine that a left hand is a dominant hand of user 3. In such an example, GUI module 10 may generate a left-handed GUI for display at display 4 including a left-handed visual configuration that is different from a right-handed visual configuration. For instance, the left-handed visual configuration may include a visual layout of graphical elements 12 such that graphical elements 12 are positioned at locations of display 4 along an arc that follows a radius reachable by a left thumb of user 3. As such, techniques of this disclosure may promote usability of computing device 2 by facilitating user selection of graphical elements with a dominant hand of a user.

Figure 1B:
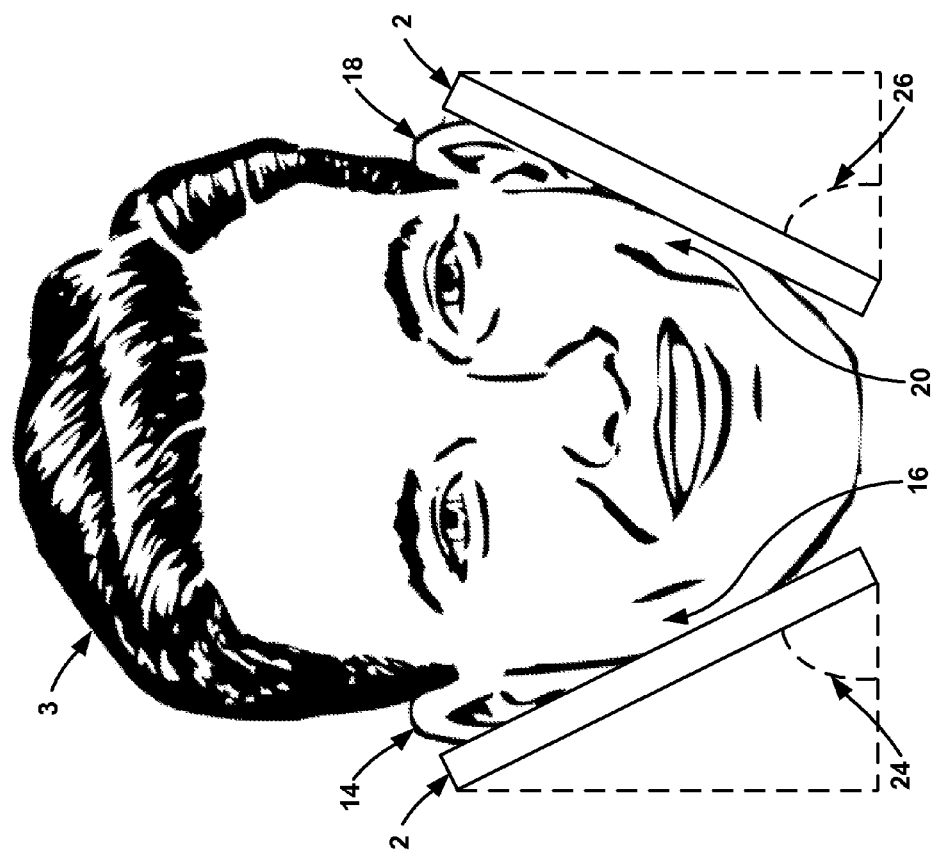
FIG. 1B is a conceptual diagram illustrating an example of the computing device of FIG. 1A that may be used to determine a dominant hand of a user and generate a graphical user interface based at least in part on the determined dominant hand, in accordance with one or more aspects of this disclosure.

FIG. 1B is a conceptual diagram illustrating an example of the computing device of FIG. 1A that may be used to determine a dominant hand of a user and generate a graphical user interface based at least in part on the determined dominant hand, in accordance with one or more aspects of this disclosure. As illustrated in the example of FIG. 1B, user 3 may use computing device 2 for telephonic communications, such as by holding computing device 2 to right ear 14 and right cheek 16 or to left ear 18 and left cheek 20. As shown in FIG. 1B, when computing device 2 is held against right ear 14 and right cheek 16, a physical orientation of computing device 2 may result in angle 24 of the physical orientation of computing device 2 with respect to the ground. In contrast, when computing device 2 is held against left ear 18 and left cheek 20, a physical orientation of computing device 2 may result in angle 26 with respect to the ground.

As illustrated, angle 24 may be different from angle 26. That is, angle 24 may be substantially opposite angle 26. Physical orientation information of computing device 2, such as information received from one or more gyroscopes or accelerometers of computing device 2, may be usable to determine the dominant hand of user 3. For instance, because user 3 may typically hold computing device 2 in a dominant hand to a dominant side of his or her head when using computing device 2 for telephonic communications, physical orientation information indicating a physical orientation of computing device 2 that is within a threshold value of angle 24 (e.g., a threshold value of one degree, five degrees, ten degrees, or other threshold values) may indicate that a right hand is a dominant hand of user 3. Similarly, physical orientation information indicating a physical orientation of computing device 2 that is within a threshold value of angle 26 may indicate that a left hand is a dominant hand of user 3.

Figure 2:
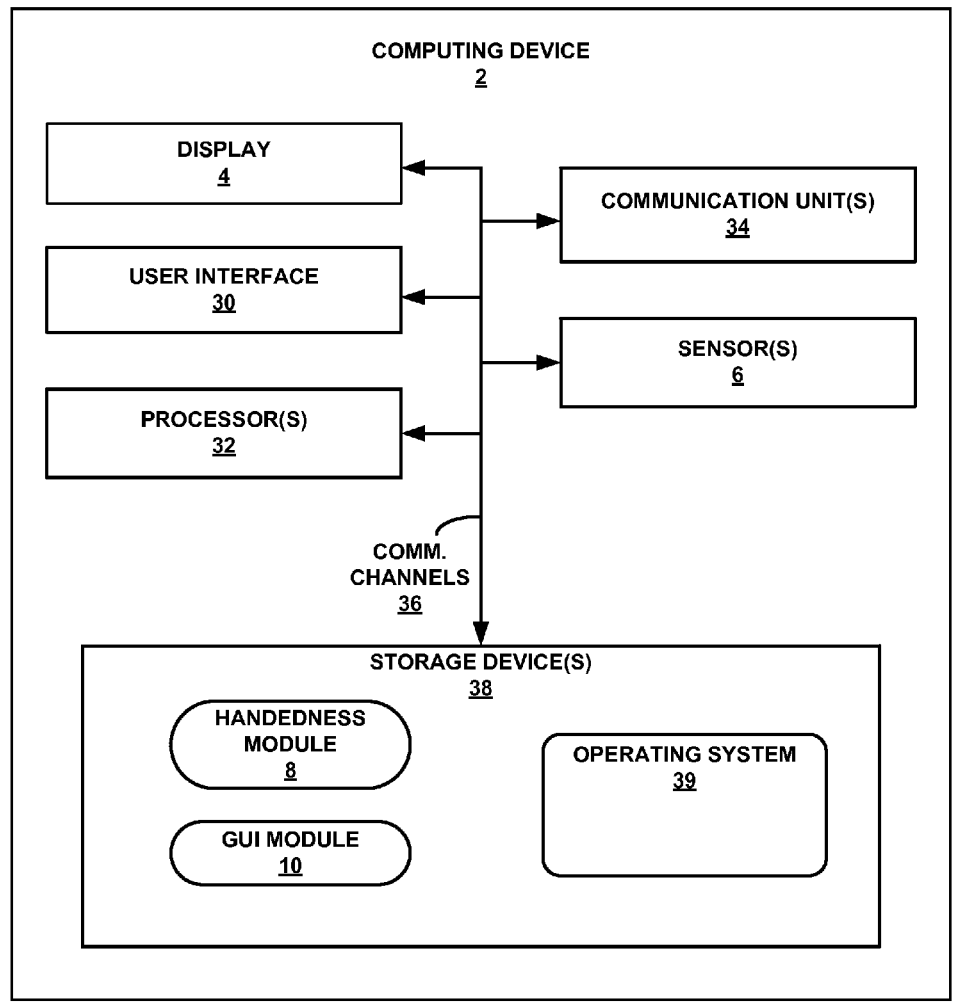
FIG. 2 is a block diagram illustrating further details of one example of a computing device shown in FIGS. 1A and 1B, in accordance with one or more aspects of this disclosure.

FIG. 2 is a block diagram illustrating further details of one example of a computing device shown in FIGS. 1A and 1B, in accordance with one or more aspects of this disclosure. FIG. 2 illustrates only one particular example of computing device 2, and many other examples of computing device 2 may be used in other instances.

As shown in the specific example of FIG. 2, computing device 2 includes display 4, user interface 30, one or more processors 32, one or more communication units 34, one or more sensors 6, and one or more storage devices 38. As illustrated, computing device 2 further includes handedness module 8, GUI module 10, and operating system 39 that are executable by computing device 2. Each of components 4, 6, 30, 32, 34, and 38 may be interconnected (physically, communicatively, and/or operatively) for inter-component communications. In some examples, communication channels 36 may include a system bus, network connection, inter-process communication data structure, or any other channel for communicating data. As one example in FIG. 2, components 4, 6, 30, 32, 34, and 36 may be coupled by one or more communication channels 36. Handedness module 8, GUI module 10 and operating system 39 may also communicate information with one another as well as with other components of computing device 2.

One or more processors 32, in one example, are configured to implement functionality and/or process instructions for execution within computing device 2. For example, one or more processors 32 may be capable of processing instructions stored at one or more storage devices 38. Examples of one or more processors 32 may include any one or more of a microprocessor, a controller, a digital signal processor (DSP), an application specific integrated circuit (ASIC), a field-programmable gate array (FPGA), or equivalent discrete or integrated logic circuitry.

One or more storage devices 38 may be configured to store information within computing device 2 during operation. One or more storage devices 38, in some examples, may be described as a computer-readable storage medium. In some examples, one or more storage devices 38 may be a temporary memory, meaning that a primary purpose of one or more storage devices 38 is not long-term storage. One or more storage devices 38 may, in some examples, be described as a volatile memory, meaning that one or more storage devices 38 do not maintain stored contents when the computer is turned off. Examples of volatile memories include random access memories (RAM), dynamic random access memories (DRAM), static random access memories (SRAM), and other forms of volatile memories known in the art. In some examples, one or more storage devices 38 may be used to store program instructions for execution by one or more processors 32. One or more storage devices 38, for example, may be used by software or applications running on computing device 2 (e.g., handedness module 8 and/or GUI module 10) to temporarily store information during program execution.

One or more storage devices 38, in some examples, also include one or more computer-readable storage media. One or more storage devices 38 may be configured to store larger amounts of information than volatile memory. One or more storage devices 38 may further be configured for long-term storage of information. In some examples, one or more storage devices 38 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

User interface 30 may allow a user of computing device 2 to interact with computing device 2. Examples of user interface 30 may include, but are not limited to, a keypad embedded on computing device 2, a keyboard, a mouse, a roller ball, buttons, or other devices that allow a user to interact with computing device 2. In some examples, computing device 2 may not include user interface 30, and the user may interact with computing device 2 with display 4 (e.g., by providing various user gestures). In some examples, the user may interact with computing device 2 with user interface 30 or display 4.

Computing device 2, in some examples, also includes one or more communication units 34. Computing device 2, in one example, utilizes one or more communication units 34 to communicate with external devices via one or more networks, such as one or more wireless networks, one or more cellular networks, or other types of networks. One or more communication units 34 may be a network interface card, such as an Ethernet card, an optical transceiver, a radio frequency transceiver, or any other type of device that can send and receive information. Other examples of such network interfaces may include Bluetooth, 3G and WiFi radio computing devices as well as Universal Serial Bus (USB). In some examples, computing device 2 utilizes one or more communication units 34 for telephonic communications with an external device.

Computing device 2 may also include one or more sensors 6. Examples of one or more sensors may include, but are not limited to, accelerometers, gyroscopes, magnetometers, audio input devices (e.g., a microphone), image sensors (e.g., an image sensor associated with a camera device of computing device 2), and proximity sensors. Computing device 2 may receive a plurality of input values from one or more sensors 6. As an example, computing device 2 may receive a acceleration information from one or more accelerometers, physical orientation information from one or more gyroscopes, physical orientation information from one or more magnetometers (e.g., physical orientation information with respect to the magnetic field of the earth), audio information from one or more audio input devices, visual information from one or more image sensors (e.g., visual information representing an anatomical feature of a user, such as an ear of the user), and proximity information from one or more proximity sensors (e.g., information indicating physical proximity of computing device 2 to another object).

Computing device 2 may include operating system 39. Operating system 39, in some examples, controls the operation of components of computing device 2. For example, operating system 39, in one example, facilitates the communication of handedness module 8 and GUI module 10 with one or more processors 32, display 4, user interface 30, one or more communication units 34, and one or more sensors 6, as described in FIGS. 1A and 1B.

In accordance with techniques of this disclosure, handedness module 8 may determine a plurality of features, each of which is usable to determine a dominant hand of a user. Handedness module 8 may receive a plurality of input values from one or more sensors 6 corresponding to the respective plurality of features. For example, handedness module 8, executing on one or more processors 32, may receive a plurality of input values from one or more sensors 6 using communication channels 36. Handedness module 8 may determine a dominant hand of the user based at least in part on the plurality of input values corresponding to the plurality of features. In response, GUI module 10 may generate a GUI for display at a display device operatively coupled to computing device 2 (e.g., display 4) based at least in part on the determination of the dominant hand.

Handedness module 8 may use a probabilistic model, such as a Bayesian network, to determine the dominant hand of the user. For example, for one or more of the plurality of input values determined from information received from one or more sensors 6, handedness module 8 may determine a difference between the respective input value and a respective baseline value. The respective baseline values may be determined, in some examples, using input values received during a ground-truth data collection phase. For instance, information from sensors (e.g., one or more sensors 6) may be collected while known right-handed and left-handed users perform various tasks using computing device 2 or other similar computing device. The baseline values may be used to determine a feature vector that represents stereotypical state information of computing device 2 (e.g., physical orientation information, acceleration information, etc.) during use by known right-handed and/or left-handed users. In certain examples, the baseline values may be modified based on information received from one or more sensors 6. For instance, a baseline value corresponding to a feature representing a stereotypical cheek-press input (e.g., a profile of an area of a presence-sensitive display that detects input indicating contact between the presence-sensitive display and a cheek of a user) may be modified based on user input information detected at display 4.

Handedness module 8 may apply a weighted value associated with the respective feature to the determined difference to generate a weighted difference value. For example, while each feature of the feature vector may be usable to determine a dominant hand of a user, certain of the features may provide a stronger indication of a dominant hand of the user. As one example, visual information including a representation of at least a portion of an ear of the user may provide a stronger indication of a dominant hand of a user than acceleration information indicating a motion of computing device 2 to a particular side of a user's head. In such an example, handedness module 8 may apply a weighted value (e.g., a coefficient) to a determined difference between visual information input values and a visual information baseline feature than to a determined difference between acceleration information input values and an acceleration information baseline feature. In some examples, handedness module 8 may apply weighted values that range between zero and one.

Handedness module 8 may aggregate the one or more weighted difference values to determine an aggregated weighted difference value. For example, handedness module 8 may determine a distance between an n-dimensional input feature vector and an n-dimensional baseline feature vector, where "n" represents the number of features in each of the input and baseline feature vectors. In certain examples, handedness module 8 may determine a representation of an angle between an n-dimensional input feature vector and an n-dimensional baseline feature vector, such as by determining the cosine of the angle between the two vectors.

Handedness module 8 may determine the dominant hand of the user based at least in part on the aggregated weighted difference value. For instance, handedness module 8 may compare the aggregated weighted difference value to a threshold value, and may determine the dominant hand of the user based on the comparison. As one example, handedness module 8 may determine that an aggregated weighted difference value that is greater than or equal to a threshold value corresponds to a right-handed user and an aggregated weighted difference value that is less than the threshold value corresponds to a left-handed user.

In certain examples, handedness module 8 may determine the plurality of features that are usable to determine a dominant hand of a user in response to one or more received inputs corresponding to a particular feature. For instance, handedness module 8 may receive an input value corresponding to a first feature. In response, handedness module 8 may determine one of an active state and an inactive state of a sensor associated with a second feature based at least in part on a criterion that specifies a relationship between the first feature and the second feature. Handedness module 8 may activate the sensor associated with the second feature in response to determining an active state of the sensor. Similarly, handedness module 8 may, in certain examples, deactivate the sensor associated with the second feature in response to determining an inactive state of the sensor.

As an example, the input value corresponding to the first feature may include an indication of a user input detected at a presence-sensitive display operatively coupled to computing device 2 (e.g., display 4). The sensor associated with the second feature may include an image sensor of the mobile computing device (e.g., an image sensor associated with a camera device of computing device 2). Handedness module 8 may determine at least one of an active and inactive state of the image sensor based at least in part on a determination that a received indication of a user input detected at the presence-sensitive display is indicative of a contact between the presence-sensitive display and at least a portion of a head of a user (e.g., a cheek-press user input). Handedness module 8 may determine an active state of the image sensor when the received indication of the user input indicates a contact between the presence-sensitive display and at least the portion of the head of the user.

Handedness module 8 may determine an inactive state of the image sensor when the received indication of the user input does not indicate a contact between the presence-sensitive display and at least a portion of the head of the user. As such, in examples where computing device 2 includes a battery to provide electrical power to components of computing device 2, handedness module 8 may help to decrease power consumption of components of computing device 2. That is, rather than require that each sensor of sensors 6 be active during use of computing device 2, handedness module 6 may activate and deactivate at least one of sensors 6 based on received inputs corresponding to a particular feature. In the above example, rather than require that a camera device of computing device 2 be active at all times to detect information associated with a portion of a user's head (e.g., at least a portion of an ear of the user), handedness module 8 may activate the camera device in response to receiving a user input at display 4 indicating that display 4 is in contact with at least a portion of the user's head. As such handedness module 8 may conserve battery power by activating the camera device in response to an input indicating that such visual information may likely be available.

Similarly, the input value corresponding to the first feature may include the indication of the user input detected at the presence-sensitive display (e.g., display 4), and the sensor associated with the second feature may include a gyroscope of computing device 2. Handedness module 8 may determine the active state of the gyroscope based at least in part on a determination that the received indication of the user input at the presence-sensitive display is indicative of a contact between the presence-sensitive display and at least a portion of the head of the user. As such, handedness module 8 may conserve battery power by activating the gyroscope in response to an input indicating that physical orientation information usable to determine the dominant hand of the user is likely available (e.g., a physical orientation of computing device 2 with respect to the ground when computing device 2 is used for telephonic communications).

As another example, the input value corresponding to the first feature may include an audio input from an audio input device (e.g., a microphone) of computing device 2. In such an example, the sensor associated with the second feature may include an accelerometer of computing device 2. Handedness module 8 may determine the active state of the accelerometer based at least in part on a determination that a received audio input is indicative of wind noise. For example, a received audio input that is indicative of wind noise may indicate movement of computing device 2. As such, handedness module 8 may decrease power consumption of accelerometers of computing device 2 by activating the accelerometers in response to determining that the received audio input indicates wind noise, and hence, possible motion of computing device 2.

FIGS. 3A and 3B are conceptual diagrams illustrating an example computing device that may be used to determine a dominant hand of a user and generate a graphical user interface based at least in part on the determined dominant hand, in accordance with one or more aspects of this disclosure. In the example of FIG. 3A, GUI module 10 generates a GUI for display at display 4 in a right-handed dominant hand visual configuration including graphical elements 40A, 40B, 40C, 40D, and 40E (collectively referred to herein as "graphical elements 40") in visual layout 42. In the example of FIG. 3B, GUI module 10 generates a GUI for display at display 4 in a left-handed non-dominant hand visual configuration including graphical elements 44A, 44B, and 44C (collectively referred to herein as "graphical elements 44") in visual layout 46.

In the example of FIG. 3A, handedness module 8 may determine that a right hand of user 3 is a dominant hand of user 3. GUI module 10 may generate a GUI including graphical elements 40 for display at display 4 based at least in part on the determination of the right hand as the dominant hand of the user. For example, as illustrated, GUI module 10 may generate the GUI in a right-handed visual configuration. The right-handed visual configuration may include a visual layout of at least one graphical element (e.g., at least one of graphical elements 40). For instance, as illustrated in FIG. 3A, GUI module 10 may generate the GUI for display such that graphical elements 40 are positioned at locations of display 4 along an arc that follows a radius reachable by a right thumb of user 3. That is, as illustrated, GUI module 10 may generate the right-handed visual configuration such that graphical elements 12 are positioned at a right portion of display 4 along an arc that follows a radius of a typical motion of a right thumb of user 3 as user 3 moves his or her right thumb between a bottom portion of display 4 and a top portion of display 4.

Similarly, in certain examples, handedness module 8 may determine that a left hand of user 3 is a dominant hand of user 3. In such examples, GUI module 10 may generate the GUI in a left-handed visual configuration. The left-handed visual configuration may include a visual layout of at least one graphical element (e.g., at least one of graphical elements 40). For example, in response to determining that a left hand of user 3 is a dominant hand of user 3, GUI module 10 may generate the left-handed GUI for display in a left-handed dominant hand visual configuration such that graphical elements 40 are positioned at locations of display 4 along an arc that follows a radius reachable by a left thumb of user 3.

The dominant hand visual configuration may be different from a non-dominant hand visual configuration. For instance, the dominant hand visual configuration may include one or more dominant hand layout properties that specify, for at least one graphical element, a visual layout of the at least one graphical element. Similarly, the non-dominant hand visual configuration may include one or more non-dominant hand layout properties that specify, for at least one graphical element, a visual layout of the at least one graphical element. The dominant-hand visual layout may be different from the non-dominant hand visual layout.

For example, as illustrated in FIG. 3A, a right-handed visual configuration (e.g., a dominant hand visual configuration in this example) may include a right-handed visual layout of at least one of graphical elements 40. In this example, the right-handed visual configuration may include one or more right-handed layout properties that specify the visual layout of graphical elements 40. The right-handed visual layout (e.g., a dominant hand visual layout in this example) may be different from a left-handed visual layout (e.g., a non-dominant hand visual layout in this example). For instance, the left-handed visual configuration may include one or more left-handed layout properties that specify a left-handed visual layout of graphical elements 40 that is different than the right-handed visual layout of graphical elements 40.

As an example, the left-handed layout properties may specify a left-handed visual layout of graphical elements 40 such that graphical elements 40 are positioned along an arc that follows a radius reachable by a left thumb of user 3. Examples of such layout properties may include, but are not limited to, a size of at least one graphical element (e.g., a size of at least one of graphical elements 40), a shape of the at least one graphical element, a display location of the at least one graphical element at a display device (e.g., display 4), and information indicating whether the at least one graphical element is displayed at the display device. Each of the dominant hand and non-dominant hand visual configuration may include such visual layout properties. In addition, one or more of the respective visual layout properties associated with each of the dominant hand visual configuration and the non-dominant hand visual configuration may be different, such that a dominant hand visual layout of the dominant hand visual configuration is different than the non-dominant hand visual layout of the non-dominant hand visual configuration.

In certain examples, handedness module 8 may determine that a user (e.g., user 3) is currently holding computing device 2 with a non-dominant hand of the user. For instance, using techniques of this disclosure, handedness module 8 may determine the dominant hand of the user based at least in part on a received plurality of input values corresponding to a respective plurality of features usable to determine a dominant hand of a user. In addition, handedness module 8 may determine, based at least in part on the plurality of input values, that a user is currently holding computing device 2 with a non-dominant hand of the user.

As an example, handedness module 8 may determine that a right hand of user 3 is a dominant hand of user 3. In addition, handedness module 8 may determine that a plurality of input values corresponding to a respective plurality of features usable to determine the dominant hand of the user indicates that the user is currently holding computing device 2 with the non-dominant hand of the user. For instance, handedness module 8 may compare an input feature vector to a baseline feature vector determined with respect to known right-handed and/or left-handed users. Handedness module 8 may determine, in some examples, that user 3 is a right-handed user, and that the input feature vector correlates to a baseline feature vector associated with known left-handed users. In such examples, handedness module 8 may determine that user 3 may be currently holding computing device with a non-dominant hand of user 3 (i.e., a left hand of user 3 in this example). Similarly, handedness module 8 may determine that user 3 is a left-handed user, and that the input feature vector correlates to a baseline feature vector associated with known right-handed user. In such examples, handedness module 8 may determine that user 3 may be currently holding computing device 2 with a non-dominant hand of user 3 (i.e., a right hand of user 3 in the current example). Responsive to determining that the user is currently holding computing device 2 with the non-dominant hand of the user, GUI module 10 may generate the GUI for display in a non-dominant hand visual configuration.

As illustrated in FIG. 3B, GUI module 10 generates a GUI in a left-handed non-dominant hand visual configuration including graphical elements 44 in visual layout 46. As illustrated, visual layout 46 (i.e., a non-dominant hand visual layout in this example) may be different than visual layout 42 (i.e., a dominant hand visual layout in the example of FIG. 3A). For instance, at least one of graphical elements 44 may correspond to at least one of graphical elements 40. However, visual layout 46 may differ from visual layout 42 with respect to at least one of a shape, a size, and a display location of the at least one corresponding graphical elements. In addition, visual layout 46 may differ from visual layout 42 with respect to whether the at least one corresponding graphical element is displayed at display device 4.

As an example, graphical elements 44 may correspond to graphical elements 40A, 40B, and 40C of FIG. 3A. For instance, graphical elements 40A and 44A may each be a "compose" graphical button to enable a user to create a new email message. Similarly, graphical elements 40B and 44B may each be "send" graphical buttons to enable a user to send an email message, and graphical elements 40C and 44C may each be "archive" graphical buttons to enable a user to archive one or more email messages. However, visual layout 46 (i.e., a non-dominant hand visual layout in this example) may be different from visual layout 42 (i.e., a dominant hand visual layout in this example) with respect to the display location of each of the corresponding graphical elements and a size of each of the corresponding graphical elements. In addition, visual layout 46 may be different from visual layout 42 in that certain graphical elements displayed in visual layout 46 may not be displayed in visual layout 46 (i.e., graphical elements 40D and 40E in this example).

As such, GUI module 10 may promote usability of computing device 2 by facilitating user selection of graphical elements with the non-dominant hand of the user. For example, to help compensate for a tendency of users to be less accurate when providing user input gestures with a non-dominant hand of the user, GUI module 10 may display fewer graphical elements in a non-dominant hand visual configuration than in a dominant hand visual configuration, each of the graphical elements of the non-dominant hand visual configuration being larger than the corresponding graphical elements of the dominant hand visual configuration.

Figure 4:
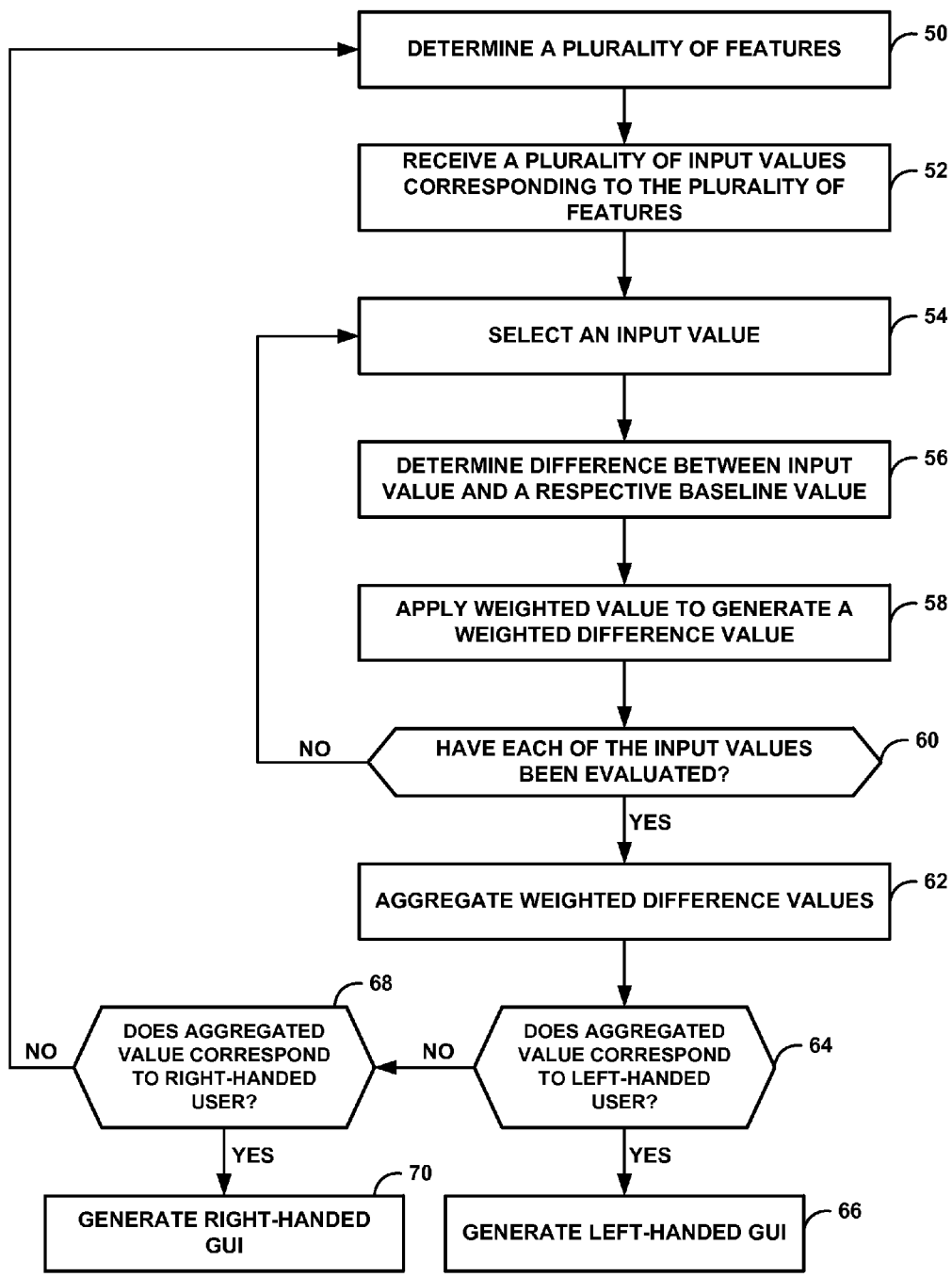
FIG. 4 is a flow diagram illustrating example operations of a computing device to determine a dominant hand of a user and output a graphical user interface based at least in part on the determined dominant hand, in accordance with one or more aspects of this disclosure.

FIG. 4 is a flow diagram illustrating example operations of a computing device to determine a dominant hand of a user and output a graphical user interface based at least in part on the determined dominant hand, in accordance with one or more aspects of this disclosure. The example illustrated in FIG. 4 is only one example operation, and other implementations may include more or fewer aspects than those depicted in FIG. 4. For purposes of illustration only, the example operations are described below within the context of computing device 2.

Handedness module 8, executing on one or more processors 32, may determine a plurality of features (50). Each feature from the plurality of features may be usable to determine a dominant hand of a user of computing device 2. Handedness module 8 may receive a plurality of input values, each input value from the plurality of input values corresponding to a respective feature from the plurality of features (52). For example, handedness module 8 may receive a plurality of input values from one or more sensors 6, each input value corresponding to a respective feature from the plurality of features. Handedness module 8 may select an input value from the plurality of input values (54). Handedness module 8 may determine a difference between the respective input value and a respective baseline value (56). Handedness module 8 may apply a weighted value associated with the respective feature to the determined difference to generate a weighted difference value (58).

Handedness module 8 may determine whether each input value of the plurality of input values has been evaluated (60). For example, handedness module 8 may determine, for each input value of the plurality of input values, whether a difference has been determined between the input value and a respective baseline value. When handedness module 8 determines that at least one of the input values of the plurality of input values has not been evaluated ("NO" branch of 60), handedness module 8 may select a next input value. When handedness module 8 determines that each input value of the plurality of input values has been evaluated ("YES" branch of 60), handedness module 8 may aggregate the weighted difference values to determine an aggregated weighted difference value (62).

Handedness module 8 may determine whether the aggregated weighted difference value corresponds to a left-handed user (64). When handedness module 8 determines that the aggregated value corresponds to a left-handed user ("YES"

branch of 64), GUI module 10 may output for display at display 4 a GUI in a left-handed visual configuration (66). In some examples, when handedness module 8 determines that the aggregated value does not correspond to a left-handed user ("NO" branch of 64), handedness module 8 may determine whether the aggregated value corresponds to a right-handed user (68). In certain examples, when handedness module 8 determines that the aggregated value does not correspond to a left-handed user, GUI module 10 may output for display at display 4 a GUI in a right-handed visual configuration. That is, rather than perform operation 68 to determine whether the aggregated value corresponds to a right-handed user, GUI module 10 may output for display at display 4 a GUI in a right-handed visual configuration as a default visual configuration, and may output a GUI in a left-handed visual configuration in response to handedness module 8 determining that the aggregated value corresponds to a left-handed user.

In certain examples, when handedness module 8 determines that the aggregated value corresponds to a right-handed user ("YES" branch of 68), GUI module 10 may output for display at display 4 a GUI in a right-handed visual configuration (70). When handedness module 8 determines that the aggregated value does not correspond to a right-handed user ("NO" branch of 68), handedness module 8 may determine a plurality of features, each of which may be usable to determine a dominant hand of a user.

In some examples, handedness module 8 may output for display at display 4 a GUI in a hand-neutral visual configuration. For instance, when handedness module 8 determines that the aggregated value does not correspond to a right-handed user ("NO" branch of 68), GUI module 10 may output for display at display 4 a GUI in a hand-neutral visual configuration. In certain examples, GUI module 10 may output for display at display 4 the GUI in the hand-neutral visual configuration and handedness module 8 may determine a plurality of features, each of which may be usable to determine a dominant hand of a user (e.g., operation 50).

A hand-neutral visual configuration may include, for example, a visual configuration that favors neither a left hand nor a right hand of a user. For instance, a hand-neutral visual configuration of a GUI may include one or more graphical elements (e.g., one or more graphical button controls) output at locations of display 4 equidistant between a typical arc of a left thumb of a user holding a mobile computing device in the left hand of the user and a typical arc of a right thumb of a user holding the mobile computing device in the right hand of the user. In some examples, one or more of a size and shape of at least one graphical element included in a hand-neutral visual configuration may be configured to favor neither a left hand nor a right hand of a user. For instance, one or more visual layout properties associated with each of a dominant hand visual configuration (e.g., a left-handed visual configuration in one example) and a non-dominant hand visual configuration (e.g., a right-handed visual configuration in one example) may define one or more of a size and shape of at least one graphical element included in the dominant hand visual configuration and the non-dominant hand visual configuration. As an example, the one or more visual layout properties may specify a particular size of a graphical element for display in the non-dominant hand visual configuration, and may specify a smaller size of the graphical element for display in the dominant hand visual configuration. In certain examples, GUI module 10 may output for display at display 4 a GUI in a hand-neutral visual configuration, such as by outputting one or more graphical elements with a size that is an average of the size of the one or more graphical elements specified by the visual layout properties associated with each of a dominant hand visual configuration and a non-dominant hand visual configuration.

In some examples, GUI module 10 may output for display at display 4 a GUI in a visual configuration specified by a user of computing device 2. For instance, a user may specify one of a right-handed, left-handed, or hand-neutral visual configuration, such as by using user interface 30 (e.g., selecting a visual configuration preference). In such examples, GUI module 10 may output for display at display 4 a GUI in a visual configuration corresponding to the user-selected visual configuration. That is, in such examples, GUI module 10 may output for display at display 4 a GUI in a visual configuration corresponding to the user-selected visual configuration regardless of determinations made by handedness module 8 based on the aggregated weighted difference values.

Figure 5:
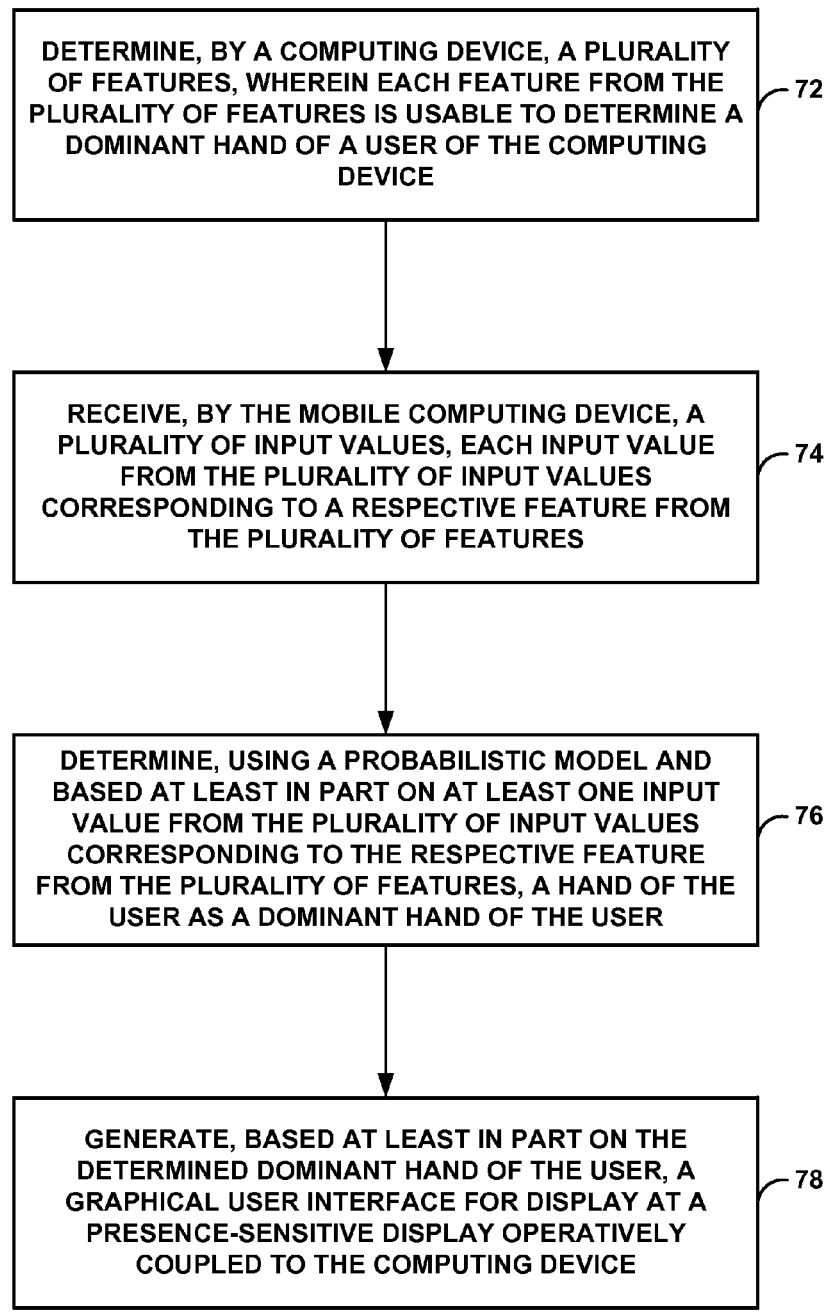
FIG. 5 is a flow diagram illustrating example operations of a computing device to determine a dominant hand of a user and output a graphical user interface based at least in part on the determined dominant hand, in accordance with one or more aspects of this disclosure.

FIG. 5 is a flow diagram illustrating example operations of a computing device to determine a dominant hand of a user and output a graphical user interface based at least in part on the determined dominant hand, in accordance with one or more aspects of this disclosure. The example illustrated in FIG. 5 is only one example operation, and other implementations may include more or fewer aspects than those depicted in FIG. 5. For purposes of illustration only, the example operations are described below within the context of computing device 2.

Computing device 2 may determine a plurality of features, wherein each feature from the plurality of features is usable to determine a dominant hand of a user of computing device 2 (72). Computing device 2 may receive a plurality of input values, each input value from the plurality of input values corresponding to a respective feature from the plurality of features (74). Computing device 2 may determine, using a probabilistic model and baed at least in part on at least one input value from the plurality of input values corresponding to the respective feature from the plurality of features, a hand of the user as a dominant hand of the user (76). Computing device 2 may generate, based at least in part on the determined dominant hand of the user, a graphical user interface for display at a display device operatively coupled to computing device 2 (e.g., a presence-sensitive display) (78).

In some examples, generating the graphical user interface based at least in part on the determined dominant hand includes generating for display the graphical user interface in a dominant hand visual configuration. The dominant hand visual configuration may be different from a non-dominant hand visual configuration. In certain examples, the dominant hand visual configuration includes a first visual layout of the at least one graphical element at the display device, the non-dominant hand visual configuration includes a second visual layout of the at least one graphical element at the display device, and the first visual layout is different from the second visual layout.

In some examples, the dominant hand visual configuration includes one or more dominant hand layout properties that specify, for the at least one graphical element, the first visual layout of the at least one graphical element, and the non-dominant hand visual configuration includes one or more non-dominant hand layout properties that specify, for the at least one graphical element, the second visual layout of the at least one graphical element. In certain examples, the one or more dominant hand layout properties include one or more of a size of the at least one graphical element, a shape of the at least one graphical element, a display location of the at least one graphical element at the display device, and information indicating whether the at least one graphical element is displayed at the display device. In some examples, the one or more non-dominant hand layout properties include one or more of a size of the at least one graphical element, a shape of the at least one graphical element, a display location of the at least one graphical element at the display device, and information indicating whether the at least one graphical element is displayed at the display device.

In certain examples, the example operations further include determining, based at least in part on the received plurality of input values corresponding to the respective plurality of features, that the user is currently holding computing device 2 with a non-dominant hand of the user; and responsive to determining that the user is currently holding the computing device 2 with the non-dominant hand of the user, generating for display the graphical user interface in the non-dominant hand visual configuration. In some examples at least one input value from the plurality of input values includes acceleration information from an accelerometer of computing device 2. In certain examples, at least one input value from the plurality of input values includes physical orientation information from a gyroscope of computing device 2. In some examples, the display device includes a presence-sensitive display, and at least one input value from the plurality of input values includes an indication of a user input detected at the presence-sensitive display.

In certain examples, at least one input value from the plurality of input values includes visual information from an image sensor of computing device 2. In some examples, the visual information includes a visual representation of an anatomical feature of a head of a user. In certain examples, the anatomical feature of the head of the user includes at least a portion of an ear of the user.

In some examples, determining the dominant hand of the user, using the probabilistic model, includes for one or more input values from the plurality of input values, determining a difference between the respective input value and a respective baseline value, and applying a weighted value associated with the respective feature to the determined difference to generate a weighted difference value. In such examples, determining the dominant hand of the user may include aggregating the one or more weighted difference values to determine an aggregated weighted difference value, and determining the dominant hand of the user based at least in part on the aggregated weighted difference value.

In certain examples, determining the plurality of features includes, in response to receiving an input value corresponding to a first feature, determining, based at least in part on a criterion that specifies a relationship between the first feature and a second feature, one of an active state and an inactive state of a sensor associated with the second feature. In such examples, determining the plurality of features may further include activating the sensor associated with the second feature in response to determining the active state of the sensor, and deactivating the sensor associated with the second feature in response to determining the inactive state of the sensor.

In some examples, receiving the input value corresponding to the first feature includes receiving an audio input from an audio input device of the computing device 2, and the sensor associated with the second feature includes an accelerometer of the computing device 2. In such examples, determining the active state of the accelerometer includes determining the active state based at least in part on a determination that the received audio input is indicative of wind noise. In certain examples, the display device includes a presence-sensitive display, receiving the input value corresponding to the first feature includes receiving an indication of a user input detected at the presence-sensitive display, and the sensor associated with the second feature includes an image sensor of computing device 2. In such examples, determining the active state of the image sensor includes determining the active state based at least in part on a determination that the received indication of the user input detected at the presence-sensitive display is indicative of a contact between the presence-sensitive display and at least a portion of a head of the user.

In some examples, the display device includes a presence-sensitive display, receiving the input value corresponding to the first feature includes receiving an indication of a user input detected at the presence-sensitive display, and the sensor associated with the second feature comprises a gyroscope of the computing device 2. In such examples, determining the active state of the gyroscope includes determining the active state based at least in part on a determination that the received indication of the user input detected at the presence-sensitive display is indicative of a contact between the presence-sensitive display and at least a portion of a head of the user. In certain examples, the portion of the head of the user may include a cheek of the user.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described. These and other examples are within the scope of the following claims.

The invention claimed is:

1. A method comprising:
    receiving, by a computing device, a plurality of input values, each input value from the plurality of input values corresponding to a respective feature from a plurality of features, wherein each feature from the plurality of features is usable to determine a dominant hand of a user of the computing device;
    determining, using a probabilistic model and based at least in part on at least one input value from the plurality of input values corresponding to the respective feature from the plurality of features, a hand of the user as a dominant hand of the user, wherein the determining comprises:
        for one or more input values from the plurality of input values, generating one or more weighted difference values;
        aggregating the one or more weighted difference values to determine an aggregated weighted difference value;
        determining the dominant hand of the user based at least in part on the aggregated weighted difference value; and
    generating, based at least in part on the determined dominant hand of the user, a graphical user interface for display at a presence-sensitive display operatively coupled to the computing device.

2. The method of claim 1, wherein generating the graphical user interface based at least in part on the determined dominant hand comprises generating the graphical user interface in a dominant hand visual configuration, wherein the dominant hand visual configuration is different from a non-dominant hand visual configuration.

3. The method of claim 2,
    wherein the dominant hand visual configuration comprises a first visual layout of the at least one graphical element at the presence-sensitive display,
    wherein the non-dominant hand visual configuration comprises a second visual layout of the at least one graphical element at the presence-sensitive display, and
    wherein the first visual layout is different from the second visual layout.

4. The method of claim 3,
    wherein the dominant hand visual configuration comprises one or more dominant hand layout properties that specify, for the at least one graphical element, the first visual layout of the at least one graphical element, and
    wherein the non-dominant hand visual configuration comprises one or more non-dominant hand layout properties that specify, for the at least one graphical element, the second visual layout of the at least one graphical element.

5. The method of claim 4,
    wherein the one or more dominant hand layout properties and the one or more non-dominant hand layout properties each respectively comprise one or more of a size of the at least one graphical element, a shape of the at least one graphical element, a display location of the at least one graphical element at the presence-sensitive display, and information indicating whether the at least one graphical element is displayed at the presence-sensitive display.

6. The method of claim 2, further comprising:
    determining, based at least in part on the received plurality of input values corresponding to the respective plurality of features, that the user is currently holding the computing device with a non-dominant hand of the user; and
    responsive to determining that the user is currently holding the computing device with the non-dominant hand of the user, generating for display the graphical user interface in the non-dominant hand visual configuration.

7. The method of claim 1, wherein at least one input value from the plurality of input values comprises acceleration information from an accelerometer of the computing device.

8. The method of claim 1, wherein at least one input value from the plurality of input values comprises physical orientation information from a gyroscope of the computing device.

9. The method of claim 1, wherein at least one input value from the plurality of input values comprises an indication of a user input detected at the presence-sensitive display.

10. The method of claim 1, wherein at least one input value from the plurality of input values comprises visual information from an image sensor of the computing device.

11. The method of claim 10, wherein the visual information comprises a visual representation of an anatomical feature of a head of a user.

12. The method of claim 11, wherein the anatomical feature of the head of the user comprises at least a portion of an ear of the user.

13. The method of claim 1, wherein generating the one or more weighted difference values comprises:
    for the one or more input values from the plurality of input values:
        determining a difference between the respective input value and a respective baseline value; and
        applying a weighted value associated with the respective feature to the determined difference to generate a weighted difference value.

14. The method of claim 1, wherein determining the plurality of features further comprises:
    in response to receiving an input value corresponding to a first feature, determining, based at least in part on a criterion that specifies a relationship between the first feature and a second feature, one of an active state and an inactive state of a sensor associated with the second feature;
    activating the sensor associated with the second feature in response to determining the active state of the sensor; and
    deactivating the sensor associated with the second feature in response to determining the inactive state of the sensor.

15. The method of claim 14,
    wherein receiving the input value corresponding to the first feature comprises receiving an audio input from an audio input device of the computing device,
    wherein the sensor associated with the second feature comprises an accelerometer of the computing device, and
    wherein determining the active state of the accelerometer comprises determining the active state based at least in part on a determination that the received audio input is indicative of wind noise.

16. The method of claim 14,
    wherein receiving the input value corresponding to the first feature comprises receiving an indication of a user input detected at the presence-sensitive display, wherein the sensor associated with the second feature comprises an image sensor of the computing device, and wherein determining the active state of the image sensor comprises determining the active state based at least in part on a determination that the received indication of the user input detected at the presence-sensitive display is indicative of a contact between the presence-sensitive display and at least a portion of a head of the user.

17. The method of claim 14, wherein receiving the input value corresponding to the first feature comprises receiving an indication of a user input detected at the presence-sensitive display, wherein the sensor associated with the second feature comprises a gyroscope of the computing device, and wherein determining the active state of the gyroscope comprises determining the active state based at least in part on a determination that the received indication of the user input detected at the presence-sensitive display is indicative of a contact between the presence-sensitive display and at least a portion of a head of the user.

18. The method of claim 17, wherein the portion of the head of the user comprises a cheek of the user.

19. A non-transitory computer-readable storage medium encoded with instructions that, when executed, cause one or more processors of a computing device to perform operations comprising:

receiving a plurality of input values, each input value from a plurality of input values corresponding to a respective feature from the plurality of features, wherein each feature from the plurality of features is usable to determine a dominant hand of a user of the computing device;

determining, using a probabilistic model and based at least in part on at least one input value from the plurality of input values corresponding to the respective feature from the plurality of features, a hand of the user as a dominant hand of the user, wherein the determining comprises:

for one or more input values from the plurality of input values, generating one or more weighted difference values;

aggregating the one or more weighted difference values to determine an aggregated weighted difference value;

determining the dominant hand of the user based at least in part on the aggregated weighted difference value; and generating, based at least in part on the determined dominant hand of the user, a graphical user interface for display at a presence-sensitive display operatively coupled to the computing device.

20. A computing device, comprising:

one or more processors; and one or more sensors, wherein the one or more processors are configured to:

receive, from the one or more sensors, a plurality of input values, each input value from the plurality of input values corresponding to a respective feature from a plurality of features, wherein each feature from the plurality of features is usable to determine a dominant hand of a user of the computing device;

determine, using a probabilistic model and based at least in part on at least one input value from the plurality of input values corresponding to the respective feature from the plurality of features, a hand of the user as a dominant hand of the user, wherein the determining comprises:

for one or more input values from the plurality of input values, generate one or more weighted difference values;

aggregate the one or more weighted difference values to determine an aggregated weighted difference value;

determine the dominant hand of the user based at least in part on the aggregated weighted difference value; and generate, based at least in part on the determined dominant hand of the user, a graphical user interface for display at a display device.

* * * * *